(12) United States Patent
Brown et al.

(10) Patent No.: US 8,761,347 B2
(45) Date of Patent: Jun. 24, 2014

(54) BEAM FILTER POSITIONING DEVICE

(75) Inventors: Christopher E. Brown, Morgan Hill, CA (US); Steven W. Prince, San Francisco, CA (US); William A. Strachan, San Francisco, CA (US); Stanley Mansfield, Sunnyvale, CA (US); Stephen Mohr, Danville, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 200 days.

(21) Appl. No.: 13/324,767

(22) Filed: Dec. 13, 2011

(65) Prior Publication Data

US 2012/0087478 A1 Apr. 12, 2012

Related U.S. Application Data

(63) Continuation of application No. 12/568,619, filed on Sep. 28, 2009, now Pat. No. 8,077,830.

(51) Int. Cl.
*G21K 3/00* (2006.01)

(52) U.S. Cl.
USPC .......................................... 378/156; 378/158

(58) Field of Classification Search
USPC .................. 378/114–116, 156–159, 204–206
See application file for complete search history.

(56) References Cited

U.S. PATENT DOCUMENTS

| | | | |
|---|---|---|---|
| 2,730,566 A | 1/1956 | Bartow et al. | |
| 4,172,979 A | 10/1979 | Morrison | |
| 4,627,089 A | 12/1986 | Menor et al. | |
| 5,917,883 A | 6/1999 | Khutoryansky et al. | |
| 5,945,684 A | 8/1999 | Lam et al. | |
| 6,353,655 B1 | 3/2002 | Siochi | |
| 6,389,108 B1 | 5/2002 | Ein-Gal | |
| 7,132,674 B2 | 11/2006 | Pastyr et al. | |
| 7,763,873 B2 | 7/2010 | Flynn et al. | |
| 7,852,990 B2 | 12/2010 | Aulbach | |
| 8,077,830 B2 | 12/2011 | Brown et al. | |
| 2002/0131556 A1 | 9/2002 | Steinberg | |
| 2003/0091146 A1 | 5/2003 | Siochi | |
| 2010/0034357 A1 | 2/2010 | Svesson et al. | |
| 2011/0057110 A1 | 3/2011 | Testa et al. | |
| 2011/0293067 A1 | 12/2011 | Stahl | |
| 2012/0043481 A1 | 2/2012 | Mansfield et al. | |
| 2014/0048727 A1 | 2/2014 | Huntzinger et al. | |

OTHER PUBLICATIONS

Cosgrove et al, "Commissioning of a micro multi-leaf collimator and planning system for stereotactic radiosurgery," Radiother Oncol. 50 (1999) 325-336.

*Primary Examiner* — Jurie Yun
(74) *Attorney, Agent, or Firm* — Houst Consulting

(57) ABSTRACT

A system includes a beam filter positioning device including a plate configured to support one or more beam filters, and one or more axes operable to move the plate relative to a beam line. A control mechanism is coupled to the one or more axes for controlling the movement of the axes and configured to automatically adjust the position of at least one of the one or more beam filters relative to the beam line.

16 Claims, 10 Drawing Sheets

BEAM FILTER POSITIONING DEVICE

CROSS REFERENCE TO RELATED APPLICATIONS

This application is a continuation of U.S. application Ser. No. 12/568,619 filed Sep. 28, 2009, now U.S. Pat. No. 8,077,830, the disclosure of which is incorporated herein by reference.

BACKGROUND

This invention relates generally to X-ray apparatuses and in particular to beam filter positioning devices and linear accelerators incorporating the same.

Linear accelerators are used in a variety of industries including in medical radiation therapy and imaging. A linear accelerator includes a treatment head that houses various components configured to produce, shape or monitor a treatment beam. For example, a target produces X-rays when it is impinged by energetic electrons. A photon flattening filter shapes X-rays to provide a uniform dose distribution across the X-ray field. An ion chamber monitors the energy, dose distribution, dose rate, or other parameters of a radiation beam. In an electron mode operation, an electron scattering foil scatters incident electrons to provide a broadened, uniform profile of a treatment beam. A field light system simulates a treatment field by illuminating e.g. an area on the surface of a patient's skin.

In conventional accelerators, exchangers are used to position electron scattering foils and photon flattening filters. Foil-filter exchangers allow switching back and forth between scattering foils and flattening filters for electron or photon mode operations. Fine precision adjustments of the foils and filters in exchangers are accomplished in the factory by manually adjusting and testing the foils and filters, which is a very time consuming process.

Conventional foil-filter exchangers do not include a target assembly or field light assembly. In conventional accelerators the targets are located in other areas of the treatment head e.g. inside the accelerator vacuum envelope. The design of target assemblies residing inside the vacuum envelop is complex due to added vacuum walls and interface considerations. Actuation of targets in vacuum is complicated. Any water leaks in target cooling systems would contaminate the vacuum envelope causing extended downtime.

A field light system includes a lamp and a mirror, and is used to facilitate patient placement for treatment by providing an intense light field that coincides with the radiation treatment field shaped by collimator jaws or other beam limiting devices. Because of space limitations and other considerations, it is unfeasible to place a lamp in the same location as the radiation source. In conventional accelerators the mirror is fixedly disposed along the beam centerline and is made of a thin film that is generally transparent to radiation or electron beams. Once being installed, the mirror and the lamp projector are manually adjusted in order to achieve the required coincidence with the X-ray field. The mirror located in the beam centerline causes scattering losses and beam contamination. The thin film materials are susceptible to degradation due to exposure to radiation, damage and optical distortion.

SUMMARY

The present invention provides a beam filter positioning device that allows for significant improvement in automation of production test procedures and operation of medical linear accelerators. It provides significant savings in both test time and occupancy of final test. The beam filter positioning device performs multiple functions in producing, shaping, or monitoring a treatment beam. For instance, the device may position a target button under an electron beam to produce X-rays in a photon mode, or retract a target out of the path of an electron beam for an electron or other modes. The device may accurately position an electron scattering foil or a photon flattening filter to shape the intensity profile of a treatment beam and provide uniform treatment fields. The device may precisely position a field light assembly in simulating a treatment beam for patient alignment. It may also retract an ion chamber from the beam centerline to provide an unimpeded path for the field light. The beam filter positioning device may be modular. It can be mounted to the treatment head of an accelerator and easily removed for repair with proper lifting fixtures. Driving mechanisms such as servo motor control may be used to perform precise movement or adjustments of various device components.

In one embodiment, a carousel assembly includes a base plate, a stage supported by the base plate and movable in a linear direction, a filter-foil assembly attached to the stage, a target assembly supported by the base plate, and an ion chamber assembly supported by the base plate. The filter-foil assembly is rotatable about an axis, movable in a linear direction with the stage, and includes a plate member adapted to support one or more photon flattening filters and one or more electron scattering foils. The target assembly includes one or more targets and is movable in a linear direction. The ion chamber assembly is movable in a linear direction.

In some embodiments, the carousel assembly may include a field light assembly having a mirror member and a light source. The mirror member is preferably supported by the filter-foil assembly, and the light source is supported by the ion chamber assembly. In a preferred embodiment, the light source includes two or more lamps each being operable to project light to the mirror member for the purposes of providing redundancy.

In some embodiments, the carousel assembly may additionally include a backscatter filter assembly attached to the filter-foil assembly.

In a preferred embodiment, a plurality of photon flattening filters are positioned in a circular or partial circular configuration having a first radius, and a plurality of electron scattering foils are positioned in a circular or partial circular configuration having a second radius different from the first radius. The second radius is preferably greater than the first radius.

In one embodiment, a carousel assembly includes a plate adapted to support one or more photon flattening filters and one or more electron scattering foils, a first linear axis operable to move the plate in a linear direction, and a rotation axis operable to rotate the plate about an axis. In a preferred embodiment, the first linear axis is operable to move the rotation axis in a linear direction. Preferably, the first linear axis and/or the rotation axis comprise a servo motor controllable by a computer.

In some embodiments, a plurality of photon flattening filters are positioned in a circular or partial circular configuration having a first radius, and plurality of electron scattering foils are positioned in a circular or partial circular configuration having a second radius different from the first radius. The second radius is preferably greater than the first radius.

In one aspect, a system comprises a beam filter positioning device and a control mechanism. The beam filter positioning device comprises a plate configured to support one or more beam filters, and one or more axes operable to move the plate relative to a beam line. The control mechanism is coupled to the one or more axes for controlling the movement of the axes and configured to automatically adjust a position of at least one of the beam filters relative to the beam line.

In another aspect, a beam filter positioning device comprises a plate configured to support one or more beam filters, and two or more axes operable to move the plate. The two or more axes may comprise a linear axis operable to translate the plate and a rotation axis operable to rotate the plate. In a preferred embodiment, the linear axis is operable to translate the rotation axis.

In a further aspect, a method of automatically adjusting a beam filter position in a radiation system comprises the steps of providing a plate and one or more beam filters supported by the plate, and moving the plate using one or more motion axes to position a beam filter relative to a beam line. A control mechanism operable by computer software is used to automatically adjust the position of a beam filter in the radiation system.

In a further aspect, a method of automatically adjusting field light in a radiation system comprises the steps of providing a field light assembly including a mirror and a light source, moving the mirror using a first motion axis and/or moving the light source using a second motion axis to provide a light field that would illuminate from a virtual light source. The moving of the mirror and/or the light source is controlled by a control mechanism operable by computer software, whereby the virtual light source position is automatically adjustable in three degrees of freedom.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION OF VARIOUS EMBODIMENTS

Figure 1A:
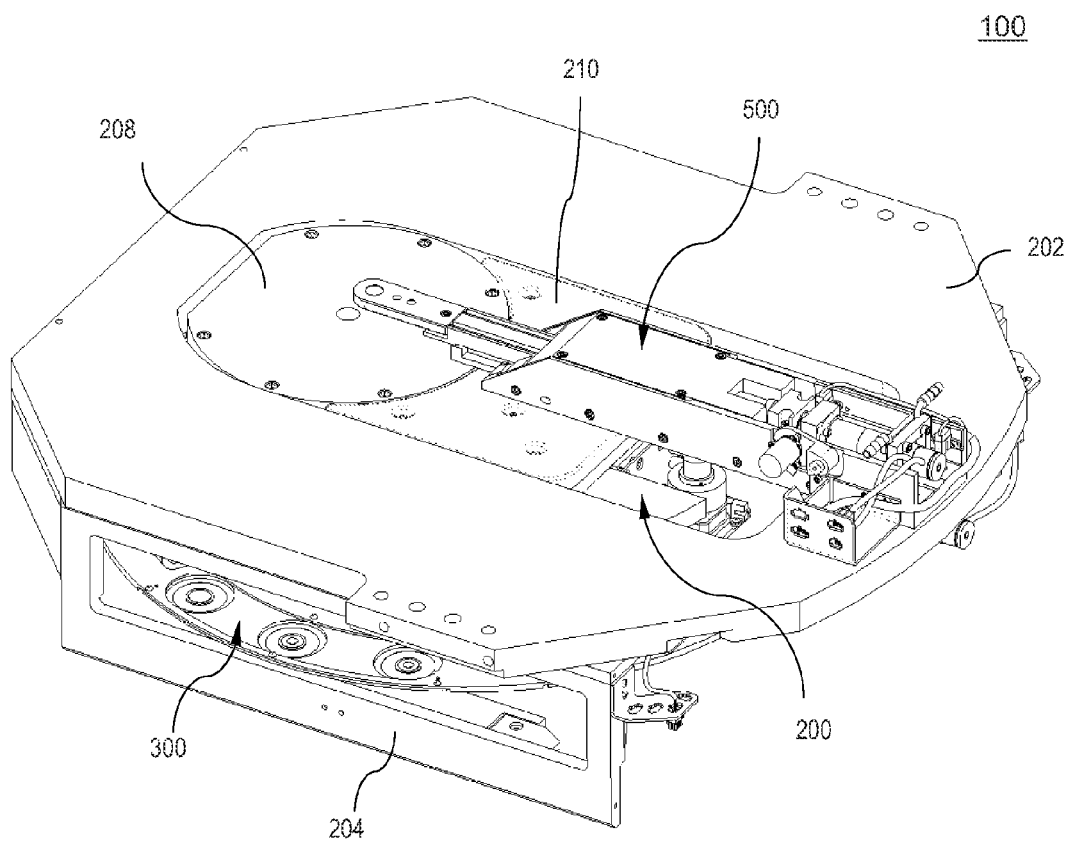
FIG. 1A is a top perspective view of a beam filter positioning device in accordance with some embodiments of the invention.

Various embodiments of beam filter positioning devices and linear accelerators incorporating the devices are described. It is to be understood that the invention is not limited to the particular embodiments described as such may, of course, vary. An aspect described in conjunction with a particular embodiment is not necessarily limited to that embodiment and can be practiced in any other embodiments. For instance, while various embodiments are described in connection with X-ray linear accelerators, it will be appreciated that the invention can also be practiced in other particle accelerators. It is also to be understood that the terminology used herein is for the purpose of describing particular embodiments only, and is not intended to be limiting since the scope of the invention will be limited only by the appended claims, along with the full scope of equivalents to which such claims are entitled. The term "carousel" is sometimes used to describe an embodiment that uses a rotational axis; but the invention is not limited to such an embodiment.

In addition, various embodiments are described with reference to the figures. It should be noted that the figures are not drawn to scale, and are only intended to facilitate the description of specific embodiments. They are not intended as an exhaustive description or as a limitation on the scope of the invention.

All technical and scientific terms used herein have the same meaning as commonly understood by one of ordinary skill in the art to which this invention belongs, unless defined otherwise. Various relative terms used in the description or appended claims such as "above," "under," "upper," "over," "on," top," "bottom," "higher," and "lower" etc. are defined with respect to the conventional plane or surface being on the top surface of the structure, regardless of the orientation of the structure, and do not necessarily represent an orientation used during manufacture or use. The following detailed description is, therefore, not to be taken in a limiting sense. As used in the description and appended claims, the singular forms of "a," "an," and "the" include plural references unless the context clearly dictates otherwise.

As used herein the term "beam filter" refers to a member that modulates one or more parameters of a particle beam such as the energy, intensity, shape, direction, dose distribution, or other beam parameters. A particle beam includes but is not limited to a beam of electrons, photons, protons, heavy ions, or other particles. By way of example, a beam filter includes but is not limited to a photon flattening filter, an electron scattering foil, and a proton scattering foil.

As used herein, the term "axis" refers to a mechanism that is operable to move an object in a direction. For example, a "linear axis" refers to a mechanism that is operable to move an object in a linear direction. A "rotation axis" refers to a mechanism that is operable to rotate an object around an axis. An axis may preferably include a servo motor and one or more feedback devices that are electrically coupled to a control mechanism operable with user interface software. A close loop control can be used to control the axis and automatically adjust the position of an object in a system.

FIGS. 1A-1D illustrate an exemplary carousel assembly or beam filter positioning device 100 in accordance with some embodiments of the invention. The device 100 may include a movable stage 200, a beam filter assembly or photon flattening filter-electron scattering foil assembly 300 (hereafter "filter-foil assembly" for simplicity of description), an ion chamber assembly 400, a field light assembly 450, and a target assembly 500. The device 100 may also include a backscatter filter 460. The movable stage 200, filter-foil assembly 300, ion chamber assembly 400, field light assembly 450, target assembly 500, and various driving mechanisms or axes are preferably coupled to or supported by a supporting structure 202 such as a frame, a base plate, or the like.

Figure 2:
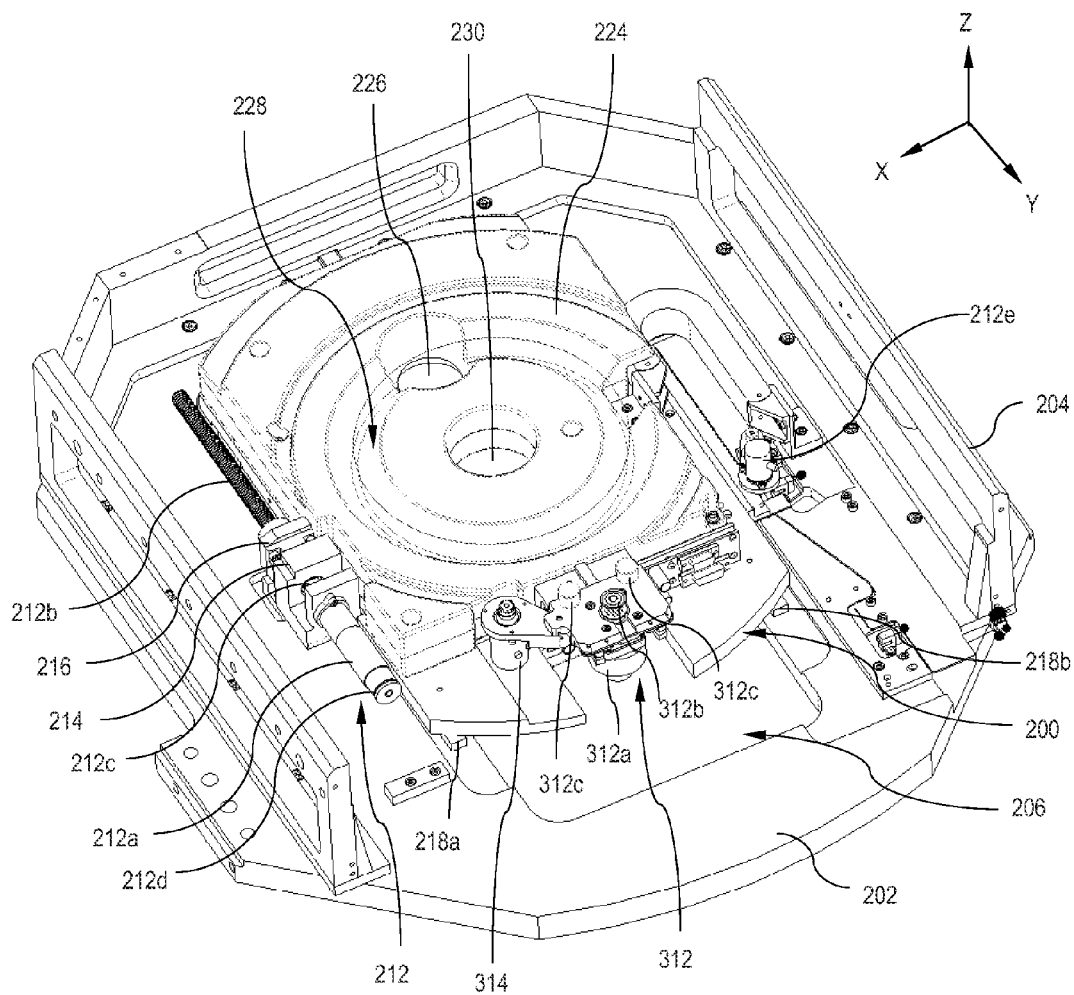
FIG. 2 is a bottom perspective view, with the beam filter assembly and the ion chamber not shown for clarity, showing a movable stage and a base plate in accordance with some embodiments of the invention.

FIG. 2 is a bottom perspective view, with the filter-foil assembly and ion chamber not shown for clarity, showing a stage 200 and a base plate 202. The base plate 202 is configured to be mounted to a treatment head and provides support for the device 100. A frame 204 is attached to the base plate 202 along its periphery providing additional support and stiffness for the device 100. The base plate 202 has a cutout 206 e.g. in a generally rectangular shape defining an open area under which the stage 200 is located.

The stage 200 supports a primary collimator 208, shielding 210, shielding 224, and filter-foil assembly 300 etc. (see also FIG. 1A), and is operable to move its payload in a direction. For example, the stage 200 can be driven by a linear axis 212 and moved along a direction such as a direction parallel to a linear accelerator plane of symmetry (Y-direction) or other directions. Alternatively, the stage 200 can be driven by a rotation axis and rotate in a direction. The linear axis 212 may include a motor 212a, a ball screw 212b, and a coupler 212c coupling the motor and the ball screw. The motor 212a and ball screw 212b can be supported by mounts 214, 216 respectively. The motor 212a serves to rotate the ball screw 212b, which is adapted to engage the stage 200 and move the stage 200 in a linear direction. Guide rails 218a, 218b fixedly attached to the base plate 202 define the linear movement of the stage 200. Slide guides or other mechanisms (not shown) can be used to engage the stage 200 with the guide rails 218a, 218b. A resolver or sensor 212d may be coupled to the motor 212a to provide primary feedback on the position of the ball screw. A housed resolver 212e may be used to provide redundant or secondary feedback. Preferably, the motor 212a is a servo motor electrically connected to a controller and operable with user interface software. While a specific motor, ball screw, guide, and feedbacks are described in detail for illustrative purposes, it should be appreciated that other types of drive mechanisms or feedbacks can also be used and anticipated by the inventors.

Figure 1B:
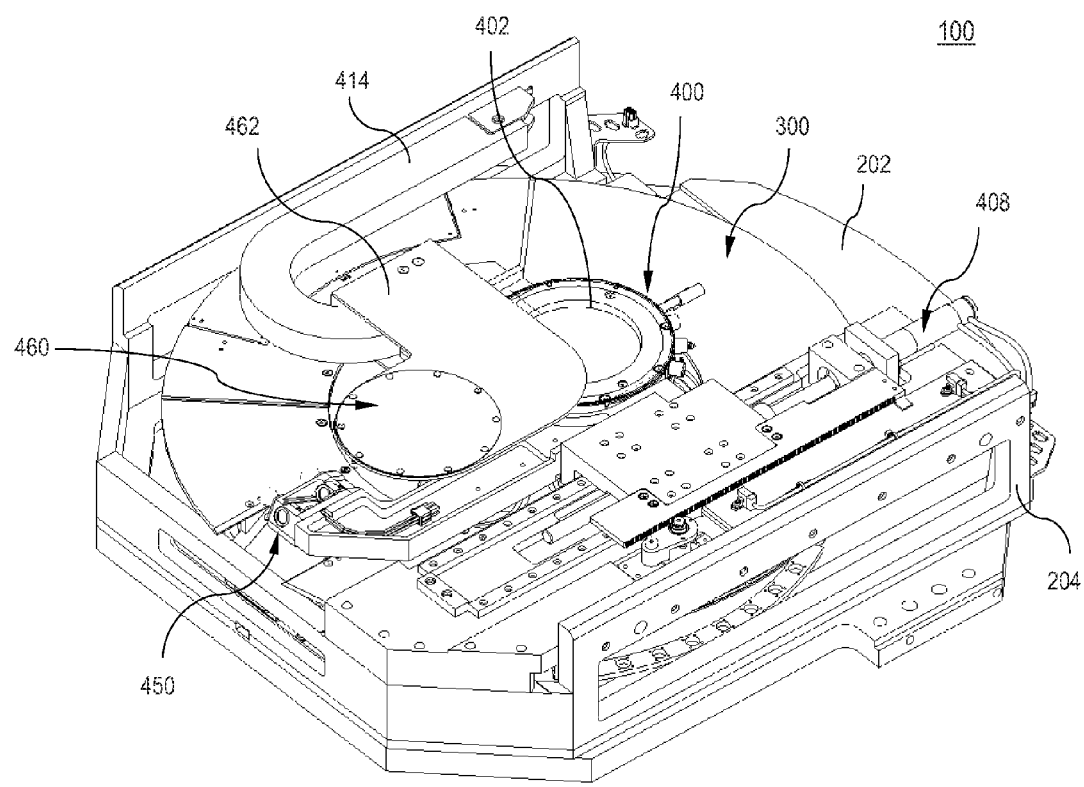
FIG. 1B is a bottom perspective view of a beam filter positioning device in accordance with some embodiments of the invention.
Figure 1C:
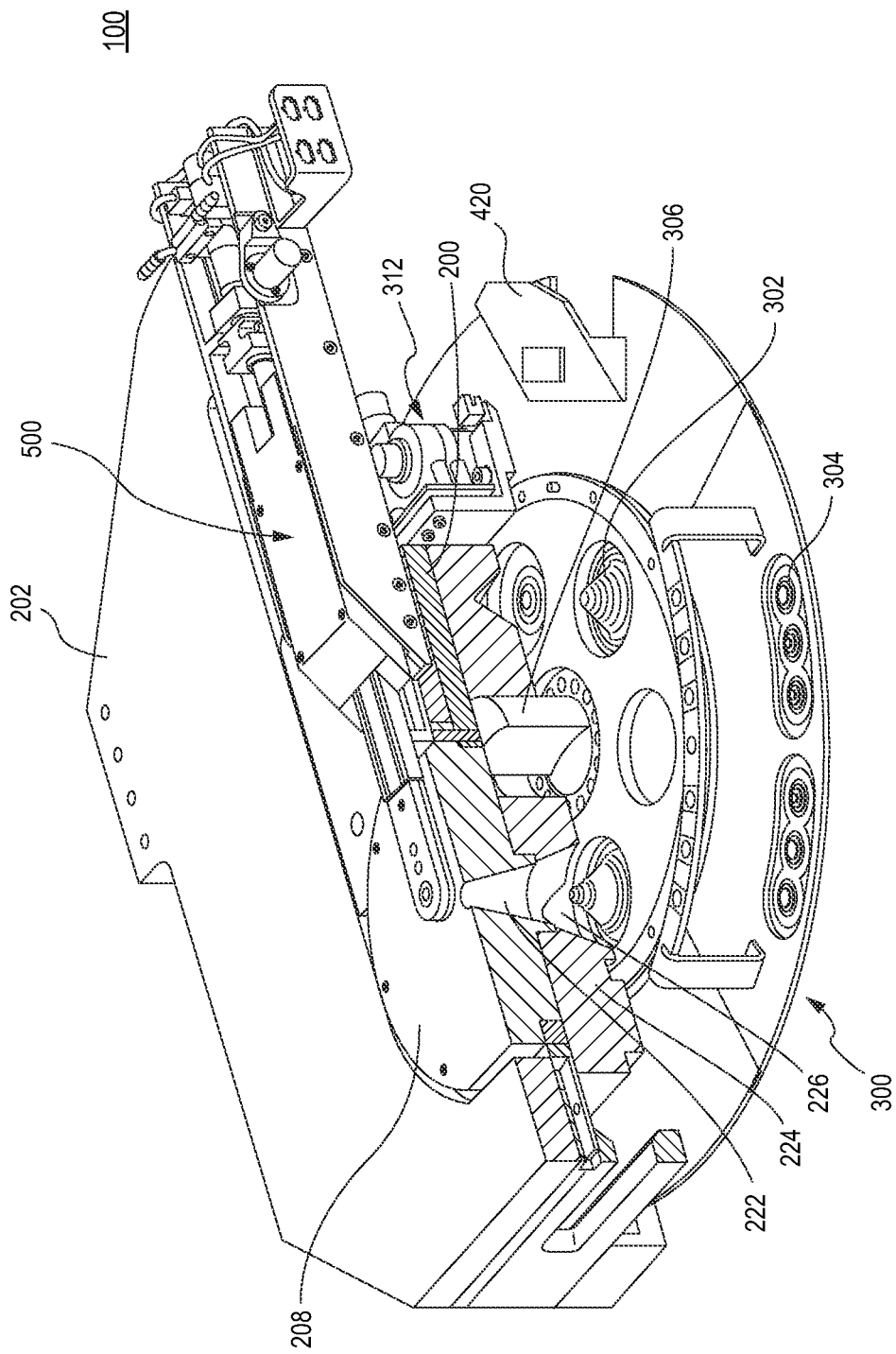
FIG. 1C is a cut-way view of a beam filter positioning device in accordance with some embodiments of the invention.
Figure 1D:
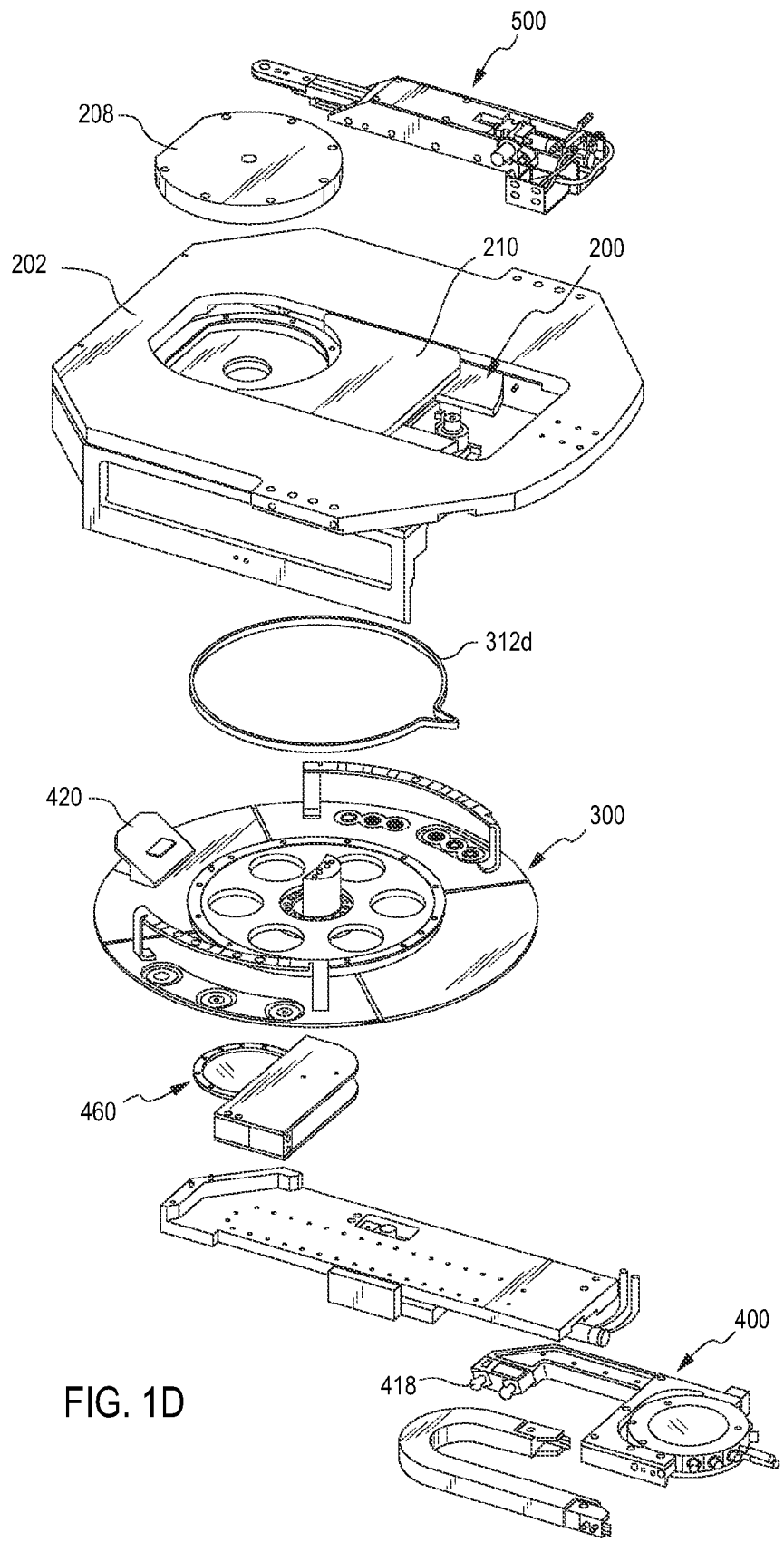
FIG. 1D is an exploded view of a beam filter positioning device in accordance with some embodiments of the invention.

The stage 200 may have an opening adapted to receive the primary collimator 208 (see also FIG. 1C). The primary collimator 208 may be provided with a step on the bottom side so that it can fit in the opening and held in place. Pins, screws, and other suitable means can be used to secure the primary collimator 208 to the stage 200. The primary collimator 208 can be made of tungsten or other suitable high density metals. The primary collimator 208 is provided with a passageway 222 (see also FIG. 1C) e.g. in a cone shape to define or shape the field of X-rays produced. Shielding 224 is located under the stage 200 and can be attached to the stage 200 via pins, screws etc. Shielding 224 is provided with a passageway 226 e.g. in a cone shape that extends from and aligns with the passageway 222 in the primary collimator 208. A circular channel 228 is provided on the bottom side of the shielding 224 to provide a travel path or clearance for photon flattening filters 302 to rotate about an axis as will be described in more detail below. A central opening 230 in the shielding 224 allows a structural member 306 passing through to fixedly attach the filter-foil assembly 300 to the stage 200 (see also FIG. 1C).

The stage 200 may be configured to support an axis such as a rotation axis 312, which is adapted to rotate or move the filter-foil assembly 300 as will be described in more detail below. For example, the stage 200 may have a U-shaped cutout at a side to provide space for the rotation axis 312. The rotation axis 312 may be supported by a bracket, which may be attached to the stage 200 by e.g. screws.

Figure 3:
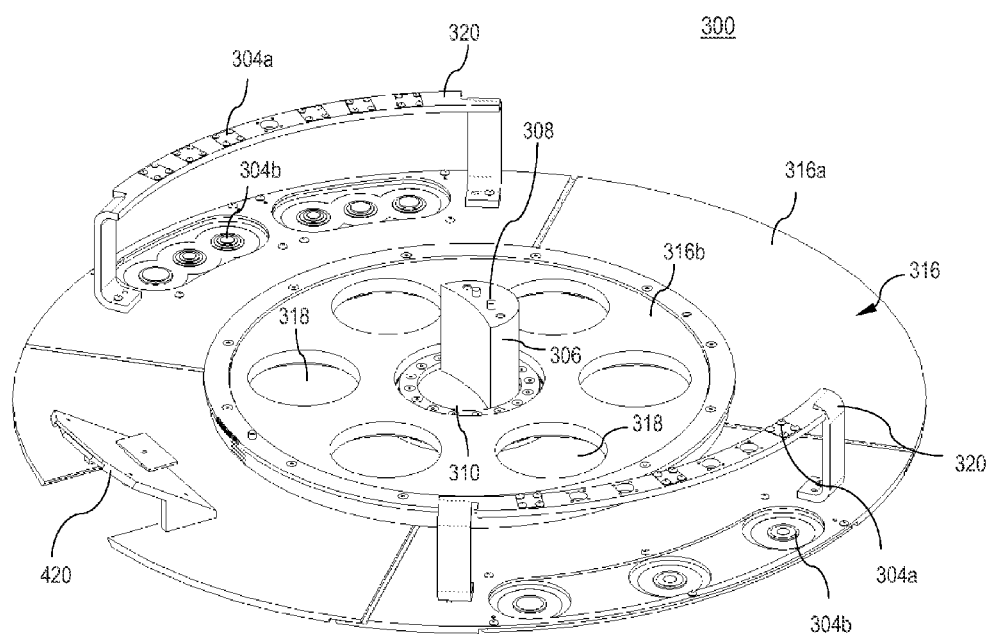
FIG. 3 is a perspective view of a beam filter assembly in accordance with some embodiments of the invention.

FIG. 3 is a perspective view of a filter-foil assembly or beam filter assembly 300 in accordance with some embodiments of the invention. For clarity photon flattening filters are not installed or shown in FIG. 3. The filter-foil assembly 300 supports one or more beam filters. For example, the filter-foil assembly 300 may support photon flattening filters 302 and electron scattering foils 304, and positions the two in photon modes and in electron modes respectively (see also FIG. 1C). The filter-foil assembly 300 is operable to move in a linear direction and rotate around an axis. Alternatively, the filter-foil assembly is operable to translate in both X- and Y-directions. The linear movement of the filter-foil assembly 300 can be accomplished by moving the stage 200 which is driven by the axis 212. The filter-foil assembly 300 can be fixedly attached to the stage 200 via a structural member 306 using e.g. pins, screws or other suitable means 308. The structural member 306 is coupled to the filter-foil assembly 300 via a bearing assembly 310 including bearing rings, bearing retainer, bearings etc. The bearing assembly 310 allows the filter-foil assembly 300 to rotate with respect to the structural member 306. The rotation of the filter-foil assembly 300 can be actuated and controlled by the rotation axis 312, which is supported by the stage 200. The rotation axis 312 includes a motor 312a, a pulley 312b, roller guides 312c, and a timing belt 312d (see also FIGS. 2, 1C, and 1D). The timing belt 312d (FIG. 1D) is wound around the pulley 312b and the filter-foil assembly plate 316b. Therefore, when actuated, the motor 312a drives the pulley 312b to turn, which transmits the rotation force to the timing belt 312d. The timing belt 312d engages filter-foil assembly plate 316b and rotates it around the structural 306. The roller guides 312c can be adjusted to control the driving force transmitted to the filter-foil assembly 300. A resolver or sensor 314 can be coupled to the motor 312a to provide primary control feedback. A second housed resolver may be used to provide redundant or secondary feedback. Preferably, the motor 312a is a servo motor electrically connected to a controller and is operable with user interface software. It should be appreciated that while a specific motor, roller guides, and feedbacks are described in detail for illustrative purposes, other types of drive mechanisms or feedback devices can also be used and anticipated by the inventors. The beam filter assembly can be driven by either a linear axis or a rotation axis, or both, or by two linear axes in X-Y directions to position a beam filter or adjust the position of a beam filter.

As illustrated in FIG. 3, the filter-foil assembly 300 includes a supporting structure 316 such as a plate or the like configured to support or position one or more beam filters such as a plurality of photon flattening filters 302 and electron scattering foils 304. For clarity photon flattening filters 302 are not shown in FIG. 3. In some preferred embodiments, the photon flattening filters 302 are positioned in a circular or partial circular configuration having a first radius. The scattering foils 304 are positioned in a circular or partial circular configuration having a second radius. The second radius is preferably different from the first radius. For example, the electron scattering foils 304 may be positioned in a partial circular configuration at locations proximate to the periphery of the plate 316, and the photon flattening filters 302 may be positioned in a circular or partial circular configuration at locations proximate to the midpoint of the radius of the plate 316.

In some preferred embodiments, the plate 316 may include a first portion 316a supporting electron scattering foils 304 or other elements, and a second portion 316b supporting photon flattening filters 302. The first and/or second portions 316a, 316b may be in a circular shape or other regular or irregular shapes. The second portion 316b may be attached to the first portion 316a by e.g. screws or other suitable means. The second portion 316b may have a plurality of ports 318 configured to receive a plurality of beam filters such as photon flattening filters 302. In FIG. 3, six ports are shown in the second portion 316b. It should be noted that a different number of ports can be provided. The photon flattening filters 302 can be in various forms including e.g. conical form, and can be held in the ports 318 by pins, screws or other suitable means. The conical filters 302 may point upwards or downwards from the plate 316. The materials, forms and/or configuration of the photon flattening filters 302 can be chosen to match the energy of the X-rays produced based on specific applications.

The electron scattering foils 304 may include primary scattering foils 304a and secondary scattering foils 304b. The combination of primary and secondary scattering foils 304a, 304b may provide a broadened, uniform profile of a treatment beam. Nine pairs of electron scattering foils are shown in FIG. 3, six grouped together on one side and three grouped together on the opposite side. It will be appreciated that a different number of electron scattering foils can be provided. The primary foils 304a may be supported by a bridge structure 320 mounted to the first plate portion 316a. The bridge structure 320 may raise the primary foils 304a above the secondary foils 304b and vertically aligns a primary foil with a secondary foil. The increased distance between the primary and secondary scattering foils allows the primary scattering foils to be higher in the treatment head and closer to the same elevation or location where the photon source (the target) is located. Having the source of electrons and the source of photons at an about same location is desirable since treatment planning and other design aspects of the treatment head are generally optimized around the location of the photon source. The increased separation between the primary and secondary electron foils also makes electron beam performance less sensitive to small machining variations in the thickness of the secondary foils and in the separation distance. An electron foil assembly with small separation between the upper and lower foils requires tighter tolerances on spacing and thickness of the lower foils to achieve uniform electron beam performance.

The linear axis 212 and rotation axis 312 or two linear axes allow for automated adjustments of the position of the electron scattering foils 304 and photon flattening filters 302. The motorized axes 212, 312 may be controlled by a computer and adjustments can be made using a software interface rather than manual adjustment as in the prior art. With a suitable 2D radiation sensor (such as a grid ion chamber array) and an automated tuning software application, these adjustments can be made without human intervention.

The use of both rotation and linear axes 212, 312 to adjust the position of electron scattering foils and photon flattening filters makes it practical to place the foils 304 and filters 302 on a different radius of a carousel assembly 300. To position the filters and foils at two different radii allows for a greater number of filters or foils available at two radii, as compared to confining both the filters and foils at a same radius. A greater selection of filters and foils may allow for a greater selection of X-ray and electron energies.

The two-radius design of filter-foil assembly 300 makes it possible that the primary collimator 208, a large piece of radiation shielding located around the photon flattening filters 302, to be absent when using electron scattering foils 304 in electron modes. The absence of the primary collimator 208 improves the performance in electron modes by reducing scatter.

The two-radius design also allows for a smaller inner radius for the flattening filters 302. A smaller inner radius of the filter travel path 228 would introduce a greater curvature in the shielding 224 gaps, hence substantially reducing the direct radiation leakage paths which would otherwise require heavy and expensive shielding plugs.

The use of a separate inner radius for filter motion allows for a large, simple and effective primary collimator 208. Prior art designs have significant compromises to the primary collimator below the target. In most prior designs, the primary collimator is fixed and chopped up in complex and inefficient ways to allow motorized filters and foils to penetrate it. Earlier designs place primary collimator shielding further from the radiation target requiring significantly greater mass, complexity and cost of shielding components.

Returning to FIG. 3, in some preferred embodiments, a mirror 420 can be installed on the filter-foil assembly 300. The mirror 420 constitutes a member of a field light assembly 450 and serves to reflect light from a light source. Because the mirror 420 is located on the filter-foil assembly 300, it can be moved out of the way of the radiation or electron beam by motorized axes 212 and 312 when it is not used in field light simulation. As a result, the mirror 420 is not required to be transparent to electron or radiation beams and can be made from any suitable materials, including a thin film or preferably a more robust material such as metal, glass etc. This is advantageous over prior art mirrors which are typically made of a thin film transparent to radiation or electron beams since it is fixedly located in the beam centerline. Thin film materials such as Mylar are more susceptible to degradation due to exposure to radiation, damage and optical distortion. They may also cause scattering losses and beam contamination.

Another benefit of disposing the field light mirror on the carousel assembly or beam filter positioning device is that the radiation shielding in the collimator assembly can be greatly simplified. In prior art accelerators, the field light mirror is typically located in the collimator assembly above the jaws, necessitating complex shielding design to allow for mounting and service of the mirror. The access allowances require shielding voids that are duplicated for symmetry, resulting in inefficient shielding requiring complicated, expensive milled pieces of shielding such as tungsten to meet shielding requirements. Without a mirror in the collimator assembly, symmetrical shape of less expensive shielding such as molded lead can be used. This would result in an improvement in electron scatter due to the more efficient shielding.

Figure 4:
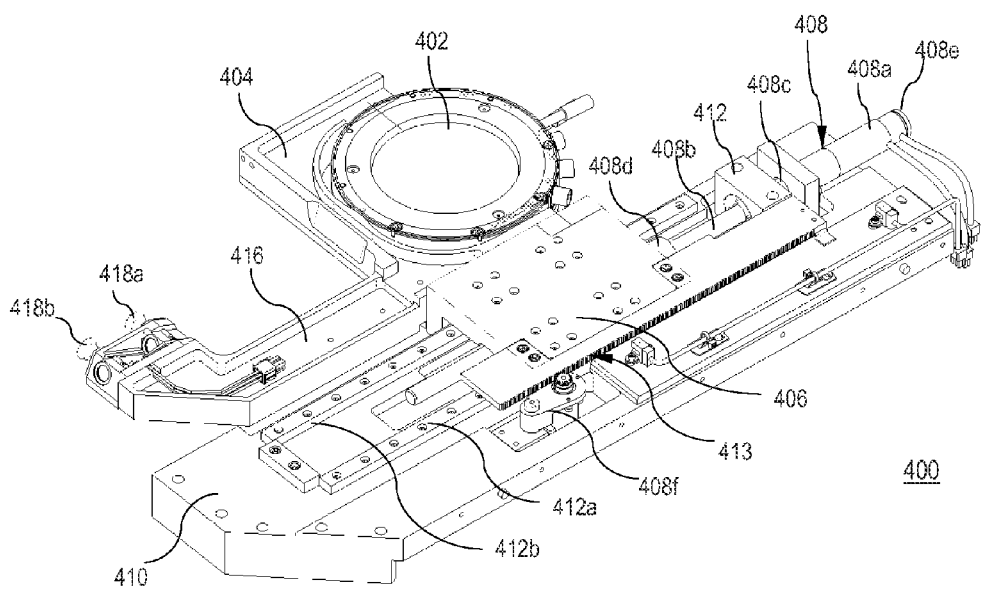
FIG. 4 is a perspective view of an ion chamber assembly in accordance with some embodiments of the invention.

FIG. 4 is a perspective view of an exemplary ion chamber assembly 400 in accordance with some embodiments of the invention. The ion chamber assembly 400 is located under the filter-foil assembly 300 for detecting the parameters of a treatment beam such as beam energy, dose distribution, and dose rate etc. The ion chamber 402 can be supported by a structural member 404 such as a bracket, which is attached to a movable member such as a plate 406. The plate 406 is driven by an axis such as a linear axis 408 which is supported by a support member such as a plate 410. The support plate 410 is attached to the base plate 202 and the frame 204. The linear axis 408 includes a motor 408a, a ball screw 408b, a coupler 408c coupling the motor and the ball screw, and a ball nut 408d engaging the ball screw. The motor 408a can be supported by a mount 412, which is attached to the support plate 410. The ball nut 408d is fixed to or otherwise engaged with the plate 406. The motor 408a serves to rotate the ball screw 408b through the coupler 408c. The ball nut 408d is engaged with the ball screw 408b and moves linearly as the ball screw 408b rotates. The plate 406 to which the ball nut 408d is fixed moves linearly as the ball nut 408d moves. Linear guide rails 412a, 412b fixedly attached to the support plate 410 define the linear movement of the plate 406. Slide guides (not shown) or other suitable mechanisms can be used to engage the plate 406 with the guide rails 412a, 412b. Therefore, when actuated, the motor 408a rotates the ball screw 408b, and moves the ball nut 408d and the plate 406 in a linear direction. The ion chamber 402, which is supported by the bracket 404 attached to the plate 406, moves with the plate 406 along the guide rails 412a, 412b in a linear direction. A cable duct 414 (see also FIG. 1B) is attached to the bracket 404 to house various cables connected to the ion chamber 402. A resolver or sensor 408e can be coupled to the motor 408a to provide primary feedback on the position of the ball screw 408b. A second housed resolver 408f may be used to provide redundant or secondary feedback. A rack and pinion gear assembly 413 may be used to provide additional feedback. Preferably, the motor 408a is a servo motor electrically connected to a controller and is operable with user interface software. It should be appreciated that while a specific motor, ball screw, and feedbacks are described in detail for illustrative purposes, other types of drive mechanisms or feedbacks can also be used and anticipated by the inventors. It should be noted that the ion chamber can be driven, positioned, or adjusted by either a linear axis or a rotation axis.

The bracket 404 may include an extension member 416. Two light sources such as filament lamps 418a, 418b can be mounted proximate to the end of the extension member 416. The light sources 418a, 418b, together with the mirror member 420 installed on the filter-foil assembly 300, forms a field light assembly 450. The extension member 416 distances the ion chamber 402 from the light sources 418a, 418b.

In a photon mode operation, the ion chamber 402 is located under a photon flattening filter 302 for detection of the parameters of a treatment beam. In an electron mode operation, the ion chamber 402 is located under an electron scattering foil in the beam centerline for detection of the parameters of a treatment beam. In field light simulation, the linear axis 408, rotation axis 312, and linear axis 212 work collectively to adjust the position of the light source 418a or 418b and mirror 420 to optically project the light source to a virtual position coincident with the same location of the radiation source. The three degree of freedom (X, Y, and Z) adjustment of the virtual light source can be accomplished by mounting the mirrors and light sources on motion axes already needed for other purposes. No additional motion axes need to be provided to achieve the three degree of freedom adjustment.

The use of motorized axes to move the lamp and mirror assemblies allows for automated adjustment of the field light system. The motorized axes can be controlled by a computer and the adjustment of the field light system can be performed using a software interface rather than the existing manual process. This would save factory adjustment time.

Because the lamp assembly 418 is mounted to a motorized axis 408, additional spare lamps can be added to the motorized axis 408 and moved into place in the event that a lamp fails. Both lamps may be factory adjusted into position relative to the assembly interface. Automatically switching to a spare lamp in the event that a light bulb fails allows a medical linear accelerator to continue to be used for treating patients until the failed lamp is replaced at a convenient time.

Referring to FIG. 1B, the beam filter positioning device 100 may further include a backscatter filter 460 located under the ion chamber assembly 400. A backscatter filter 460 such as a thin tantalum filter passes high energy photons in the beam direction, but stops low energy photons primarily caused by upward scatter off the upper collimator jaws located downstream. The backscatter filter 460 can greatly reduces unwanted backscattered radiation into the ion chamber 400. This scattered radiation has an unwanted effect on the calibration of the ion chamber 402.

The backscatter filter 460 can be supported by a structure 462, which can be fixedly attached to the bottom portion of the structural member 306 e.g. with screws. The backscatter filter 460 can therefore be moved together with the filter-foil assembly 300 in a direction. Preferably the backscatter filter 460 is positioned to have a radius from the structural member 306 about the same as for the photon flattening filters 302, so that when in an electron mode, the backscatter filter 460, like the photon flattening filters 302, can be moved out of the path of an electron beam. Preferably, the structure 462 is a box-like structure having an upper plate and a lower plate with the backscatter filter 460 being attached to the lower plate. The box-like structure 462 is preferably side open to allow the ion chamber 402 passing though the structure 462 between the upper and lower plates. In some embodiments, the backscatter filter 460 can be moved by a rotation axis.

Figure 5:
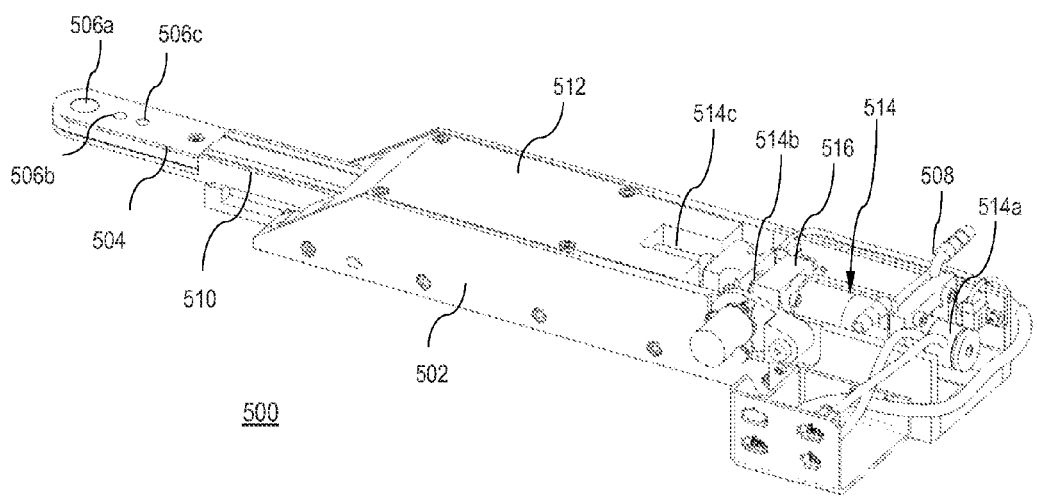
FIG. 5 is a top perspective view of a target assembly in accordance with some embodiments of the invention.

FIG. 5 is a perspective view of an exemplary target assembly 500 in accordance with some embodiments of the invention. The target assembly 500 positions a target in the beam path for generation of X-rays in a photon mode, or moves a target out of the beam path in an electron mode. The target assembly 500 can be fixedly attached to the base plate 202 via a channel mount 502. The target assembly 500 includes a substrate 504 supporting one or more target buttons 506 and a cooling tube 508 coupled to the substrate 504 for supplying a cooling fluid. Channels can be provided in the substrate 504 adjacent or surrounding the target buttons 506 for circulating a cooling fluid to dissipate heat generated during target operation. The substrate 504 and the cooling tube 508 can be supported by a mount assembly 510, which is movable relative to the channel mount 502. A shielding block 512 is placed atop and attached to the mount assembly 510 by e.g. screws or pins.

The target assembly 500 can be moved by a linear axis 514. The linear axis 514 includes a motor 514a, a ball screw (not shown), a coupler 514b coupling the motor and the ball screw, and a ball nut 514c engaging the ball screw. The motor 514a can be supported by mount 516, which is attached to the channel mount 502. The ball nut 514c is fixed to or otherwise engaged with shielding block 512. The motor 514a serves to rotate the ball screw through the coupler 514b. The ball nut 514c is engaged with the ball screw and moves linearly as the ball screw rotates. As a result, the shielding block 512, to which the ball nut 514c is fixed, moves linearly as the ball nut moves. The mount assembly 510, which supports the substrate 504 and cooling tube 508 and is attached to the shielding block 512, moves linearly as the ball nut 514c moves. Linear guide rail (not shown) fixedly attached to the channel mount 502 defines the linear movement of the mount assembly 510. Slide guides (not shown) can be used to engage the mount assembly 510 with the guide rail. A resolver or sensor can be coupled to the motor 514a to provide primary feedback on the position of the ball screw. A second housed resolver may be used to provide redundant or secondary feedback. Preferably, the motor 514a is servo motor electrically connected to a controller and is operable with user interface software. It should be appreciated that while a specific motor, ball screw, and feedbacks are described in detail for illustrative purposes, other types of drive mechanisms or feedbacks can also be used and anticipated by the inventors. It should also be noted that the target assembly can be driven, positioned, or adjusted by either linear axis or a rotation axis.

The target assembly 500 may include one or more targets each being optimized to match the energy of an incident electron beam. For example, the target assembly 500 may include a first target 506a adapted for a first photon mode, a second target 506b for a second photon mode, and a third target 506c for a third photon mode. The material of a target can be chosen and/or the thickness of a target be optimized for an incident electron beam with a particular energy level. By way of example, a first target 506a may be optimized for an incident electron beam having an energy level ranging from 4 to 6 MV. A second target 506b may be optimized for an incident electron beam having an energy level ranging from 8 to 10 MV. A third target 506c may be optimized for an incident electron beam having an energy level ranging from 15 to 20 MV. It should be noted that a different number of targets may be included in the target assembly 500. In operation, the linear axis 514 moves or positions one of the targets 506 in the beam path for a photon mode. In an electron mode, the linear axis 514 removes the targets 506 out of the beam path to allow an electron beam passes unimpeded.

Figure 6:
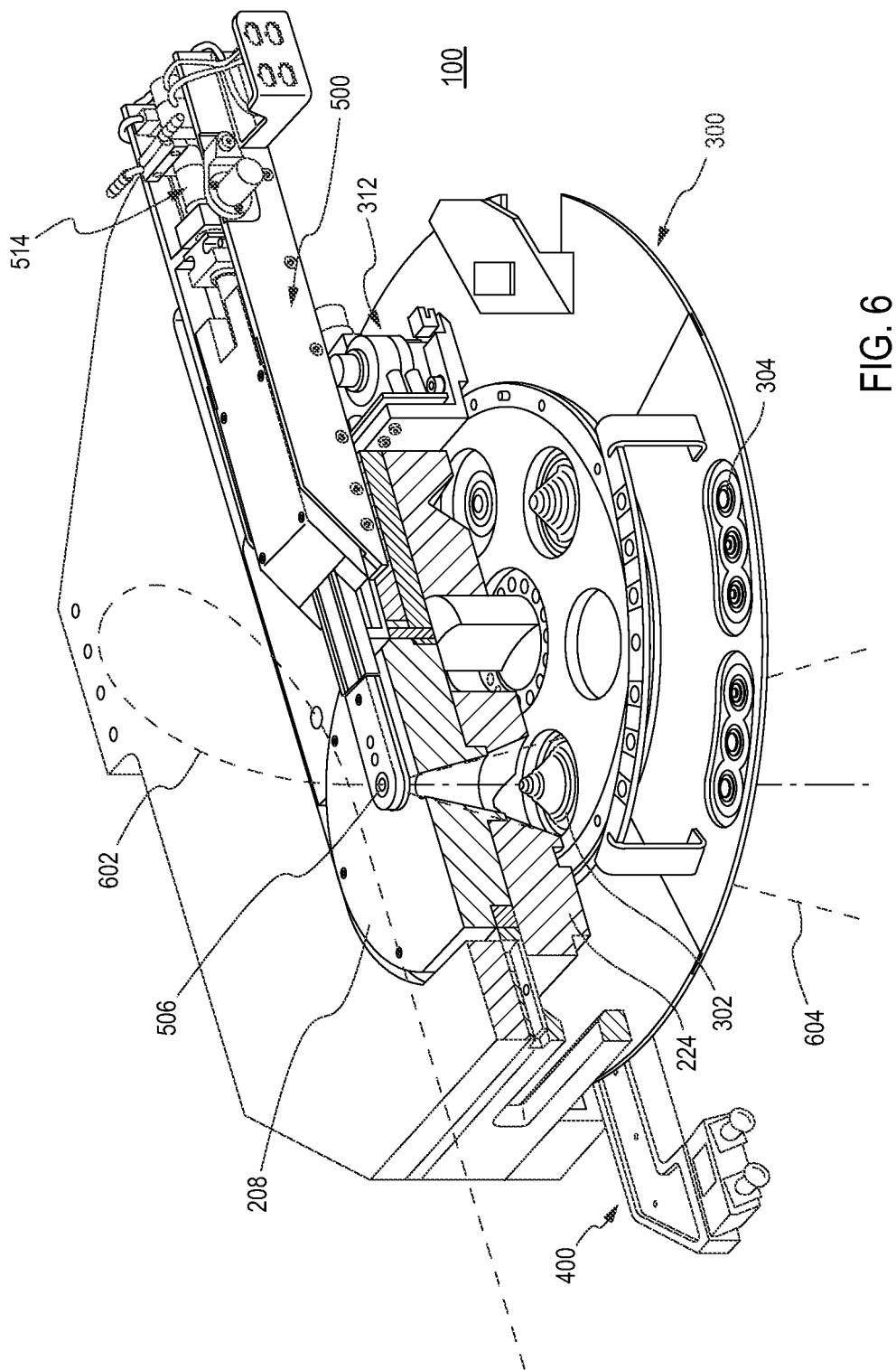
FIG. 6 is a cut-way view of a beam filter positioning device in a photon mode in accordance with some embodiments of the invention.

FIG. 6 illustrates an exemplary beam filter positioning device or carousel assembly 100 in a photon mode operation in accordance with some embodiments of the invention. The primary collimator 208 and shielding 224 have been positioned and aligned in the beam centerline. The ion chamber 402 and the backscatter filter 460 have also been positioned in the beam centerline. Rotation axis 312 is actuated to rotate the filter-foil assembly 300 clockwise or counter-clockwise to align one of the photon flattening filters 302 in the beam centerline. Sequentially or simultaneously, the linear axis 514 is actuated to position a target button 506 in the beam centerline. An electron beam 602 impinges the target button 506 and X-rays 604 are produced. The field of X-rays 604 is shaped as the X-rays produced pass through the passageways in the primary collimator 208 and shielding 224. A radiation beam with a uniform dose distribution is obtained as the X-rays pass through a flattening filter 302. The parameters of the treatment beam are detected as the beam passes through the ion chamber 402. Backscatter filter 460 located under the ion chamber 402 blocks backscatter radiation from entering the ion chamber 402 to ensure accurate measurement of the radiation beam parameters. Because the mirror 420 is installed on the filter-foil assembly 300 and is off the beam centerline in the photon mode, the treatment beam generated pass downstream unimpeded by the mirror. Depending on the energy of an incident electron beam 602 for a particular application, the linear axis 514 may move the target assembly 500 to position a target button 506 this is optimized for such beam energy in the beam path for optimized performance of the target. Similarly, depending on the energy of an incident electron beam, the rotation axis 312 may rotate to position a flattening filter 302 that is optimized for such beam energy in the beam centerline for optimized performance of the filter.

Figure 7:
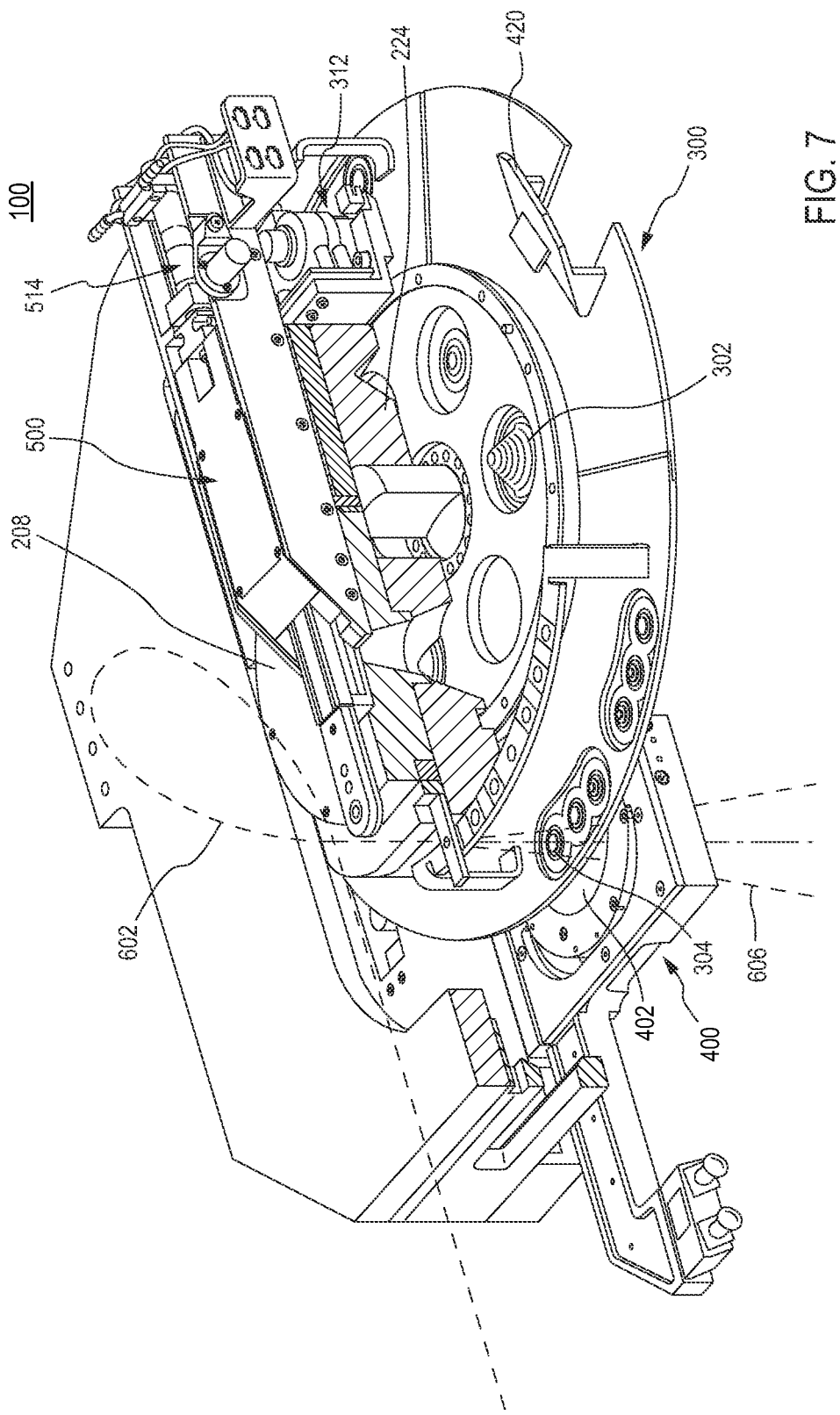
FIG. 7 is a cut-way view of a beam filter positioning device in an electron mode in accordance with some embodiments of the invention.

FIG. 7 illustrates an exemplary beam filter positioning device or carousel assembly 100 in an electron mode in accordance with some embodiments of the invention. In an electron mode, linear axis 514 is actuated and drives the target assembly 500 to move the target 506 away from the beam centerline. Linear axis 214 is actuated and drives the stage 200 to move the primary collimator 208, shielding 224, and backscatter filter 460 away from the beam centerline. Because the electron scattering foils 304 have a different or greater radius than the photon flattening filters 302 on the filter-foil assembly 300, driving the filter-foil assembly 300 to move the flattening filters 302 away from the beam centerline would bring the scattering foils 304 to the beam centerline. Rotation axis 312 is actuated and the filter-foil assembly 300 rotates clockwise or counterclockwise to align one of the electron scattering foils 304 with beam centerline. The primary and secondary scattering foils 304 scatter the electron beam to produce a broadened, uniform profile of a treatment beam 606. Depending on the energy of an incident electron beam for a particular application, the rotation axis 312 may rotate the filter-foil assembly 300 to align a scattering foil that is optimized for such beam energy in the beam path for optimized performance of the foil. The parameters of the treatment beam are detected as the beam passes through the ion chamber 402.

Figure 8:
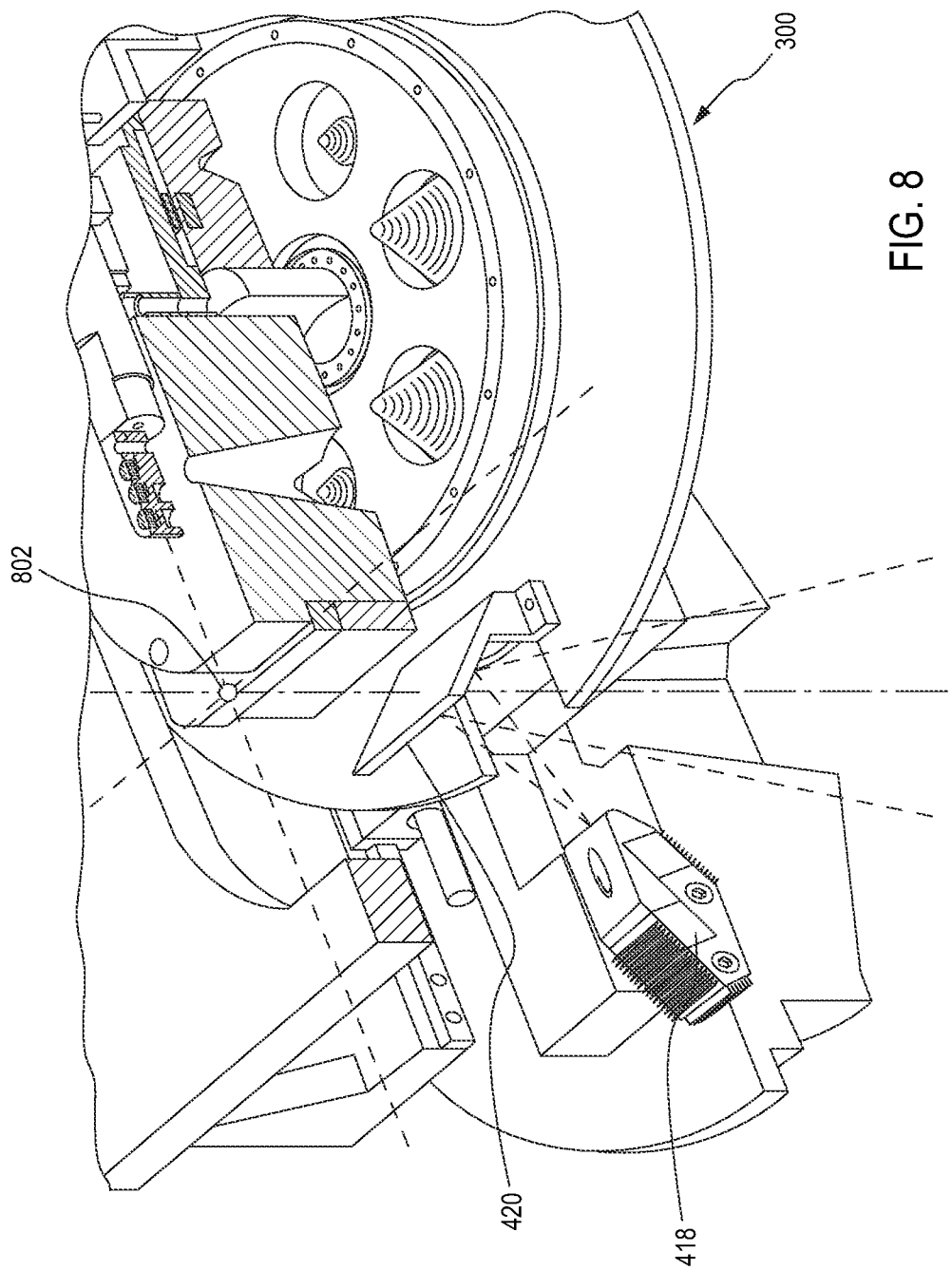
FIG. 8 is a cut-away view of a beam filter positioning device in a field light simulation mode in accordance with some embodiments of the invention.

FIG. 8 illustrates an exemplary beam filter positioning device or carousel assembly in a field light simulation mode in accordance with some embodiments of the invention. Linear axis 408 is actuated and drives the ion chamber assembly 400 to move the ion chamber 402 away from the beam centerline. Linear axis 214 is actuated and drives the stage 200 to move the primary collimator 208, shielding 224, and backscatter filter 460 away from the beam centerline. Because the mirror member 420 has a greater radius than the photon flattening filters 302 on the filter-foil assembly 300, driving the filter-foil assembly 300 to move the flattening filters 302 away from the beam centerline would bring the mirror member 420 to the beam centerline. Rotation axis 312 is actuated and rotates the filter-foil assembly 300 clockwise or counterclockwise to position the mirror member 420 in the beam centerline. The linear axis 408 moves and adjusts the position of a lamp 418 to project the lamp filament to a virtual radiation source position 802. Mirror 420 reflects light projected from the lamp 418 to illuminate an area e.g. on the surface of a patient's skin for simulation.

One of the advantages of the beam filter positioning device of the invention is that it can be configured to automatically adjust the position of beam filters, field light assembly, or other device components. The automatic adjustment can be accomplished by a control system operable by a computer software interface such as a Graphical User Interface (GUI). The control system may include a processor such as for example, a digital signal processor (DSL), a central processing unit (CPU), or a microprocessor (μP), and a memory coupled to the processor. The memory serves to store programs for the operation of the beam filter positioning device and other programs. The processor executes the program and generates signals for operation of the motion axes or other components of the beam filter positioning device. Responsive to the signals from the control system, the beam filter positioning device operates in which one or more motion axes move the beam filters, field light source, mirror, or other device components in a controlled and automatic manner based on a plan or routine, or based on a demand input from a user. The control system also receives feedback signals from sensors or resolvers in the motion axes, or from other device components such as the ion chamber, and generates signals for adjustment when necessary. For example, based on the beam parameter signals provided by the ion chamber to the control system, the control system may recalculate and generate signals for adjustment to the motion axes. The motion axes respond and automatically adjust the position of the beam filters. Similarly, based on the field light image or information, the control system may recalculate and generate signals for adjustment to the motion axes. The motion axes respond and automatically adjust the position of the light source and/or mirror to adjust the virtual light source position in three degrees of freedom.

Exemplary embodiments of beam filter positioning devices or carousel assemblies have been described. Those skilled in the art will appreciate that various modifications may be made within the spirit and scope of the invention. All these or other variations and modifications are contemplated by the inventors and within the scope of the invention.

What is claimed is:

1. A modular assembly comprising:
    a base member;
    a stage member movable relative to the base member;
    a filter-foil device coupled to and thereby moveable with the stage member, said filter-foil device comprising a body, one or more photon flattening filters and one or more electron scattering foils supported by the body, the body being movable relative to the stage member in positioning the photon flattening filters or electron scattering foils; and
    a target device supported by the base member, said target device comprising a substrate and one or more targets supported by the substrate, the substrate being movable in positioning the one or more targets.

2. The modular assembly of claim 1 which comprises:
    a first driving device supported by the base member, the first driving device being operable to move the stage member and the filter-foil device coupled to the stage member relative to the base member;
    a second driving device supported by the stage member, the second driving device being operable to move the body of the filter-foil device; and
    a third driving device supported by the base member, the third driving device being operable to move the substrate supporting the one or more targets of the target device.

3. The modular assembly of claim 2 which further comprises:
    an ion chamber device; and
    a fourth driving device supported by the base member, the fourth driving device being operable to move the ion chamber device relative to the base member.

4. The modular assembly of claim 3 which further comprises a field light device, the field light device comprising a mirror member supported by and thereby being movable with the body of the filter-foil device, and one or more light sources supported by and thereby movable with the ion chamber device.

5. The modular assembly of claim 3 wherein at least one of the first, second, third, and fourth driving devices comprises a servo motor and one or more feedback devices.

6. The modular assembly of claim 3 wherein each of the first, second, third, and fourth driving devices comprises a servo motor and one or more feedback devices.

7. The modular assembly of claim 1 wherein the one or more photon flattening filters are arranged in an arc or a circular configuration having a first radius, and the one or more electron scattering foils are arranged in an arc or a circular configuration having a second radius that is different from the first radius.

8. The modular assembly of claim 1 wherein the stage member is movable relative to the base member in a linear direction, and the body of the filter-foil device is movable at least in a rotary direction.

9. A system comprising a beam filter positioning device and a controller operable to control the beam filter positioning device using a computer software embodied in a non-transitory computer readable medium, wherein the beam filter positioning device comprises:
    a base member;
    a stage member movable relative to the base member;
    a filter-foil device coupled to and thereby moveable with the stage member, said filter-foil device comprising a body, one or more photon flattening filters and one or more electron scattering foils supported by the body;
    a first driving device supported by the base member and being operable to move the stage member and thereby the filter-foil device coupled to the stage member relative to the base member; and
    a second driving device supported by the stage member and being operable to move the body of the filter-foil device and thereby the photon flattening filters and electron scattering foils supported by the body relative to the stage member; and
    wherein the first and the second driving devices are controllable by the controller using the computer software.

10. The system of claim 9 wherein each of the first and second driving devices comprises a servo motor and one or more feedback devices which are coupled to the controller, and the controller is operable to control the servo motor based on at least signals from the one or more feedback devices.

11. The system of claim 10 wherein the beam-filter positioning device further comprises:
    a target device supported by the base member, the target device comprising a substrate and one or more targets supported by the substrate; and
    a third driving device supported by the base member and operable to move the substrate and thereby the one or more targets supported by the substrate;
    wherein the third driving device comprises a servo motor and one or more feedback devices which are coupled to the controller, and the controller is operable to control the servo motor of the third driving device based on at least signals from the one or more feedback devices of the third driving device.

12. The system of claim 11 wherein the beam-filter positioning device further comprises:
    an ion chamber device; and
    a fourth driving device supported by the base member, the fourth driving device being operable to move the ion chamber device relative to the base member;
    wherein the fourth driving device comprises a servo motor and one or more feedback devices which are coupled to the controller, and the controller is operable to control the motor of the fourth driving device based on at least signals from the one or more feedback devices of the fourth driving device.

13. The system of claim 12 which further comprises a field light device, the field light device comprising a mirror member supported by and thereby being movable with the body of the filter-foil device, and one or more light sources supported by and thereby movable with the ion chamber device.

14. The system of claim 12 wherein the controller is operable to control:
    the first driving device to move the stage member in a linear direction;
    the second driving device to move the body of the filter-foil device in a rotary direction;
    the third driving device to move the substrate in a linear direction; and
    the fourth driving device to move the ion chamber device in a linear direction.

15. The system of claim 9 wherein the one or more photon flattening filters are arranged in an arc or a circular configuration having a first radius, and the one or more electron scattering foils are arranged in an arc or a circular configuration having a second radius that is different from the first radius.

16. The system of claim 9 wherein the controller is operable to control:
- the first driving device to move the stage member in a linear direction;
- the second driving device to move the body of the filter-foil device in a rotary direction.

* * * * *